(12) United States Patent
Puckeridge

(10) Patent No.: US 6,339,421 B1
(45) Date of Patent: Jan. 15, 2002

(54) GRAPHICAL DISPLAY

(75) Inventor: Larry Puckeridge, Marrickville (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/364,742

(22) Filed: Jul. 30, 1999

(30) Foreign Application Priority Data

Jul. 31, 1998 (AU) .............................................. PP4931

(51) Int. Cl.$^7$ ................................................ G09G 5/00
(52) U.S. Cl. .......................... 345/170; 345/44; 345/82
(58) Field of Search ............................. 345/82, 44, 46, 345/55, 170, 172, 102; 313/500, 505

(56) References Cited

U.S. PATENT DOCUMENTS

| 4,113,347 A | * | 9/1978 | Gaertner |
| 4,254,453 A | * | 3/1981 | Mouyard et al. |
| 4,306,716 A | * | 12/1981 | James et al. ................... 345/82 |
| 4,485,377 A | * | 11/1984 | Claus et al. ................... 345/82 |
| 4,551,717 A | * | 11/1985 | Dreher ........................ 345/170 |
| 4,603,496 A | * | 8/1986 | Latz et al. ................... 313/500 |
| 4,804,890 A | * | 2/1989 | Havel .......................... 345/82 |
| 5,034,602 A | * | 7/1991 | Garcia, Jr. et al. ........... 345/170 |
| 5,043,716 A | * | 8/1991 | Latz et al. ..................... 345/82 |
| 5,760,754 A | * | 6/1998 | Amero, Jr. et al. ............ 345/82 |
| 5,927,274 A | * | 7/1999 | Servidio et al. |

FOREIGN PATENT DOCUMENTS

EP 0 056 335 7/1982

* cited by examiner

Primary Examiner—Regina Liang
(74) Attorney, Agent, or Firm—Pillsbury Winthrop LLP

(57) ABSTRACT

An apparatus for administering continuous positive the airway pressure to a patient includes a housing, a switch provided on the housing, and a graphical display. The graphical display includes a matrix of surface-mounted light-emitting electrodes mounted on a printed circuit board for selective illumination in response to information generated by operation of the apparatus. A display which may include an electrical switch of the apparatus or display panel, has a light emitting display surface and a plurality of light conduits transmitting light from a respective portion of be LED matrix to a portion of the display device. The information generated by operation of the device is graphically displayed by the display device.

9 Claims, 2 Drawing Sheets

GRAPHICAL DISPLAY

BACKGROUND OF THE INVENTION

The present invention relates to graphical displays for apparatus, for example control units for medical equipment such as units far administration of continuous positive airway pressure (CPAP) to a patient having means for display of information generated by operation of the apparatus.

In electrically operated apparatus, it may be desired to display status information on the housing of the apparatus in order to facilitate user operation. In its simplest form, such information may be displayed by a single light emitting diode (LED) which lights up or flashes in a particular sequence to convey the information. An example of this is flashing of an LED to indicate the number of messages on a telephone answering machine. Using a single LED limits the amount of information which may be conveyed or, to increase the amount of information, the manufacturer must resort to cryptic codes which are difficult for the user to remember.

More information can be displayed by toe of an array of LEDs or a liquid crystal display (LCD), which may be arranged in the familiar 7-segment display commonly used to reproduce alphanumeric characters in Roman script.

Known types of graphical displays include LCDs, multi-segment LEDs and surface-mounted LEDs, the latter having a matrix of LEDs mounted directly to the surface of a printed circuit board (PCB).

The surface-mounted LEDs have advantages over LCDs, and multi-segment LEDs both in terms of lower component costs and facility for automated assembly, and thus, for large scale manufacture, lowest assembly cost. However, surface-mounted LEDs have the disadvantage of being difficult to read unless mounted close to the surface of the apparatus housing. An example of this may be seen in U.S. Pat. No. 5,703,625 to Snider et al.

Snider et al provides translucent buttons and an adjacent display lens in front of a graphical display device such as an LCD or LED array. The common graphical display device is employed to provide both fixed images displayed through the buttons to indicate their function and variable information indicating the status of the system through the lens.

SUMMARY OF INVENTION

The present invention seeks to provide a low-cost alternative to the prior art.

In a first form, the present invention provides, in electrically operated apparatus, a graphical display capable of displaying information generated by operation of the apparatus, including a printed circuit board, a plurality of surface-mounted light emitting diodes arranged in a matrix on the surface of the printed circuit board, means for selectively illuminating said light emitting diodes in response to information generated by operation of the apparatus, display means including a light transmitting display surface and a plurality of elongate light conduit means for transmitting light from a respective portion of said matrix of fight emitting diodes to a portion of said display surface, such that said information generated by operation of the apparatus is displayed graphically by said display surface.

Preferably, the display means includes a respective light conduit means for each of the light emitting diodes. Preferably also, the graphical display on the display surface is arranged in a like matrix to The matrix of light emitting diodes.

Preferably, the light conduit means are integrally formed with the display means and, most preferably, are integrally moulded with the display surface.

In a further form of the invention, the display surface is included in a switch operating member of an electrical switch of the apparatus. Preferably, the apparatus further includes means responding to switch operation to cause display of said information by said switch.

Preferably the apparatus includes a plurality of such switches, and the results of the operation of one or more such switches are displayed by another such switch or switches.

Preferably the graphical display means far each switch includes a plurality of said light emitting diodes individually controllable for the generation of images such as letters, numerals or symbols or combinations thereof.

BRIEF DESCRIPTION OF THE DRAWINGS

Further preferred embodiments of the invention are described with reference to the accompanying drawings, in which.

DETAILED DESCRIPTION OF THE PREFERRED EMBODIMENTS

Figure 1:
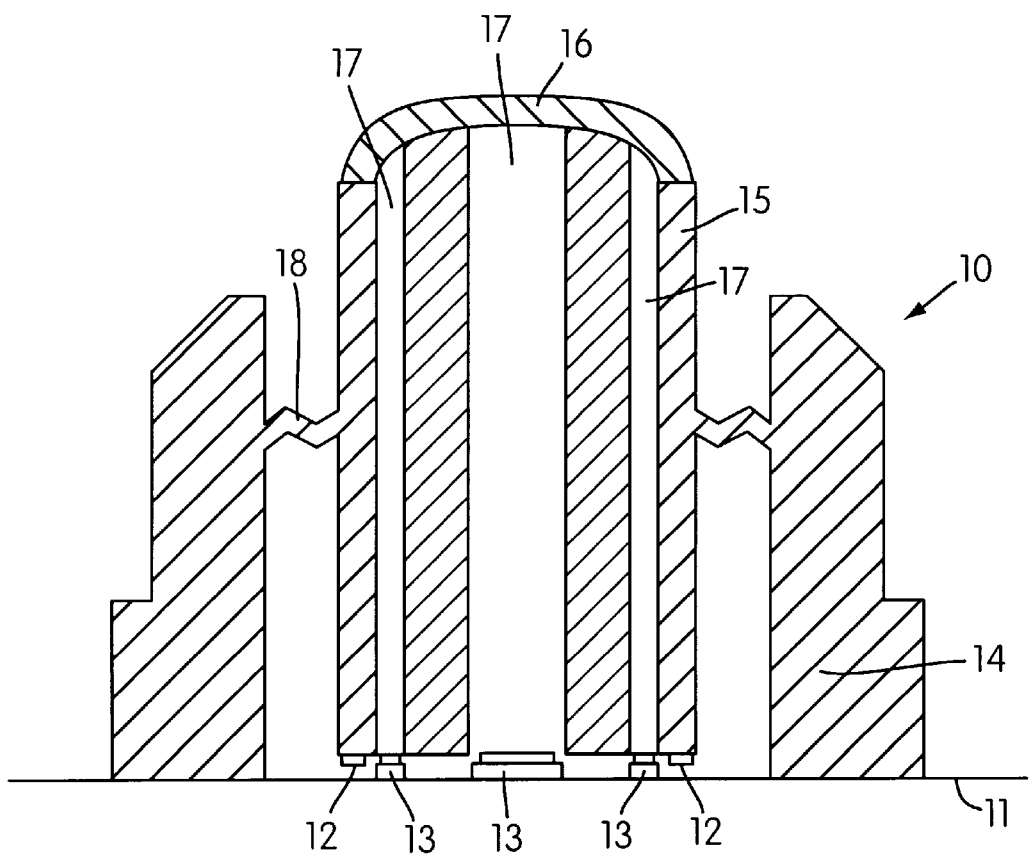
FIG. 1 is a schematic elevational cross-section of a switch incorporating a graphical display according to a first embodiment of the invention.

FIG. 1 illustrates in schematic cross-section a switch 10 incorporating one form of the present invention The switch is mounted on a printed circuit board 11 located within the body of the apparatus, the circuit board providing both the connections between the switch contacts 12, and the remainder of the circuitry of the apparatus in which the switch is employed, and also the signals by which a pattern of surface-mounted light-emitting diodes (LEDs) 13 are illuminated.

Figure 2:
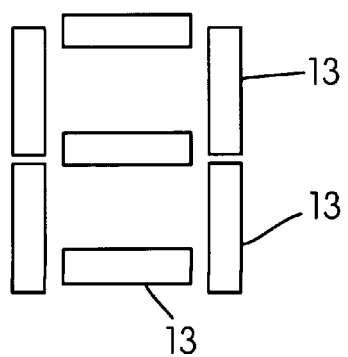
FIG. 2 shows the arrangement of the LEDs.

As shown in FIG. 2, the LEDs 13 are arranged, in this embodiment, in the seven-segment configuration commonly used to enable the reproduction of letters and numerals by selective illumination of the diodes as determined by display components not shown here.

The switch includes a body 14 fixed to the printed circuit board 11. Within the body 14 there is provided a push button member 15 which is attached to the body by means of a flexible diaphragm 18, enabling the button member to move towards the printed circuit board when pressed by the operator. The switch contacts 12, mounted at the foot of the button member, are thus pressed against stationary contacts provided on the printed circuit board.

Between the LEDs 13 and the opposite end, of the button member the latter is provided with light conduits, which may be cavities in the button member or other forms of light conduits such as fibre optic cables, and the upper face of the button member is closed by a light transmitting display surface, such as a transparent or translucent layer 16. This layer is sufficiently light transmissive that images generated by selective illumination of the LEDs 13 will be visible at the switch surface. For example, the value of an operating parameter of the apparatus may be displayed, subsequently changed and the new parameter value displayed on the same switch.

Many arrangements of the LEDs and light conduits are possible. The light conduits may be, for example, a series of holes 17 through the length of the switch, each of the holes aligned with a respective one of the LEDs. The interior walls of the light conduit may be coated with a reflective material to reduce light losses.

Depending on the ultimate shape of the switch, light from the LEDs may be visible on the front surface of the switch, or on the side surface of the switch. The display may be hooded to prevent viewing from certain angles.

The LEDs may be arranged in a matrix suitable for displaying characters (letters, numbers or punctuation marks) in the Roman script. In other embodiments of the invention, other combinations of LEDs may be used for displaying characters from other scripts, for example, the letters or numbers in Greek, Cyrillic, Japanese or Chinese. The LEDs may also be arranged so that they are capable of representing other symbols, or a plurality of symbols, such as characters from one or more scripts.

The button may be constructed from a single piece of an injected moulded plastic material, such as silicone. Alternatively, the switch may consist of several pieces. One possible construction would be for the majority of the switch to be dark plastic but with the top layer to be a light coloured or clear plastic.

It will be understood that the invention is not limited to any particular switch mechanism or mode of actuation. The switch may operate as a push button, lever or toggle switch, for example, or may have no moving pads and operate, for example, by touch.

An example of the manner of use of a switch in accordance with the FIGS. 1 and 2 will now be described, in the form of a medical instrument for the administration of continuous positive airway pressure (CPAP) to a patient used in the treatment of sleep apnea. Such a device is described, for example, in Sullivan et al. U.S. Pat. No. 5,245,995. The switch would be suitable for use in CPAP apparatus such as the ResMed Sullivan V flow generator and ventilatory assist apparatus such as the ResMed VPAP II variable pressure flow generator. References herein to a "CPAP device" are to be understood as including a reference to any of the abovementioned devices, or similar devices.

Mode of Operation for Controlling a CPAP Device

Two buttons, $B_1$ and $B_2$, would be required to control a basic CPAP device. Each button would be capable of displaying a single letter or number. The CPAP device may have several modes, for example: (1) normal mode, (2) patient hours mode, (3) pressure set mode and (4) pressure calibrate mode. By pressing the buttons in a specified way, the user may switch between modes, read parameters, set parameters and calibrate the device. No other display would be required.

Normal Mode

Normal mode is the default mode when turning on the CPAP device. The buttons will display no information. Pressing $B_1$ once will start the CPAP device and pressing it again will stop it. Pressing $B_2$ will start the CPAP device at a low flow, building up to the maximum pressure over 10 minutes (a so-called "delay timer", as described in Sullivan et at. U.S. Pat. No. 5,199,424).

Patient Hours Mode

Patient hours mode will be entered by pressing $B_2$ for at least four seconds. At that point, button $B_1$ will display patient hours, by cycling through a series of numbers, each series separated by the letter "H". Each character may be displayed for the appropriate length of time, for example one second, before changing to the next character. For example, "123" hours would be depicted by first displaying "1", then "2", then "3" and finally "H", before repeating the pattern. When the CPAP device is in patient hours mode, pressing $B_2$ will do nothing. Pressing $B_1$ will cause the device to switch to the normal mode.

Pressure Set Mode

The pressure set-point if the CPAP device is the maximum therapeutic operating pressure of the device. This pressure may range from 4 to 16 cm $H_2O$ and hence up to 2 digits needs to be displayed, the tens (the "high" digit) and the ones (the "low" digit). Pressure set mode will be entered by pressing $B_1$ for at least four seconds. $B_1$ will then display the high digit of the pressure set-point and $B_2$ will then display the low digit of the pressure set-point. Whilst in pressure set mode, pressing $B_1$ will cause low digit to increment the pressure point by 1 cm $H_2O$, and pressing $B_2$ will cause the device to decrement the pressure set-point by 1 cm $H_2O$. Pressing $B_1$ and $B_2$ simultaneously will save the current set-point and return the device to the normal mode.

Pressure Calibrate Mode

It may periodically be necessary to calibrate the pressure output of the CPAP device. Pressure calibrate mode will be entered by pressing $B_1$ and $B_2$ simultaneously for at least four seconds. The buttons will display the calibration pressure. For example, the button $B_1$ will then display "1" and the button $B_2$ will display "0". A manometer is required to measure the actual output pressure. The intended output pressure of the CPAP device may, for example, be 10 cm $H_2O$—the calibration pressure—whilst in this mode. If the output pressure is not at the required calibration pressure, the output pressure needs to be adjusted. Pressing $B_1$ will cause the CPAP device to increment pressure and pressing $B_2$ will cause the CPAP device to decrement pressure. To save this calibration and exit to the normal mode $B_1$ and $B_2$ are pressed simultaneously again.

Figure 3:
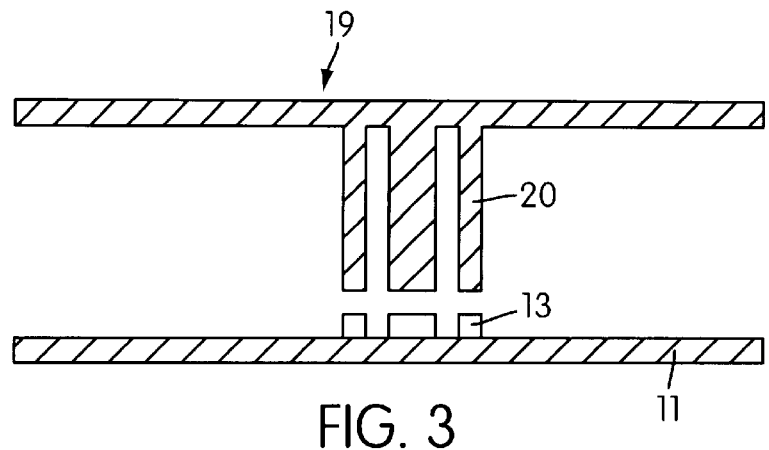
FIG. 3 is a schematic elevational cross-section of a display according to a second embodiment.

FIGS. 3 and. 4 illustrate a graphical display adapted for incorporation in the housing of an electrically operated device, separate from the control switches.

The display incorporates an integrally moulded body of light transmissive plastics material, such as polycarbonate or acrylic resin, having a display panel 19 adapted to form part of the exterior of the device and a matrix of seven light conduits 20, formed as elongate rectangular—section projections, extending from the rear of the display panel. The light conduits 20 are arranged in the same seven-segment pattern (see FIG. 4) as are the surface-mounted LEDs 13 on the printed circuit board. Light from each LED 13 travels along the respective light conduit 20 by internal reflection to the corresponding portion of the display panel 19, so that the pattern formed by selectively illuminating do LEDs is replicated on the display surface of the display panel. The exterior of each light conduit 20 may be coated and/or polished to assist the internal reflection, thus reducing light losses.

Figure 4:
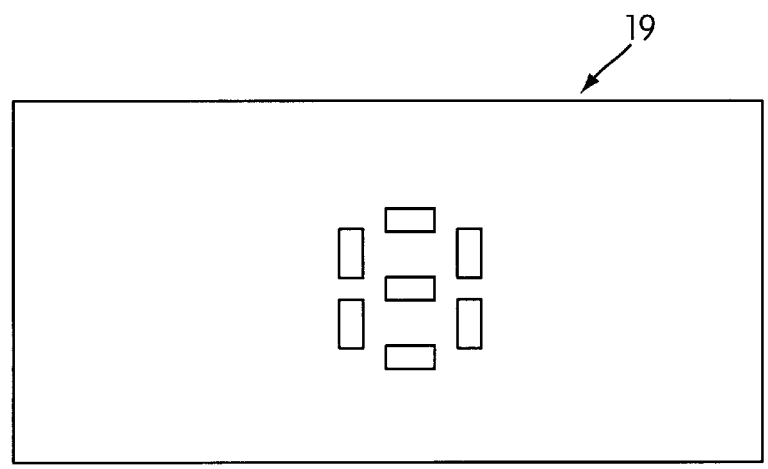
FIG. 4 is a plan view of the display of FIG. 3.
Figure 5:
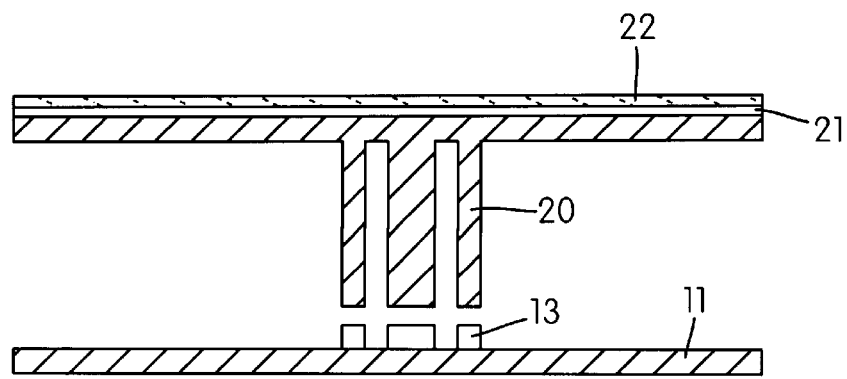
FIG. 5 is a schematic elevational cross-section of a third embodiment.

FIG. 5 shows a modification of FIGS. 3 and 4, in which the display surface of display panel is masked with an opaque, screen printed layer 21 with seven rectangular portions non-printed portions corresponding to the positions of the seven LEDs, thus concentrating light transmission at the required portions of the display. Overlying the printed layer is a top layer 22 of clear plastics, such as polycarbonate, forming a laminated construction.

While particular embodiments of this invention have been described, it will the evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. An apparatus for administering continuous positive airway pressure to a patient, comprising:
 a housing;
 at least one switch provided on the housing and including a switch operating member; and
 a graphical display integrally formed with the switch operating member, the graphical display including:
 a printed circuit board,
 a plurality of surface-mounted light-emitting diodes arranged in a matrix on a surface of the printed circuit board, and
 a display including a light transmitting display surface provided as part of the switch operating member and a plurality of elongate light conduits integrally formed with the display and structured to transmit light from a respective portion of said matrix of light emitting diodes to a portion of the display surface such that information generated by operation of the apparatus is displayed graphically on the display surface,
 wherein said switch operating member is associated with said plurality of said light conduits, each of said plurality of light conduits being provided with a respective one of said plurality of light-emitting diodes, said display surface being provided as part of said switch operating member and including a plurality of display portions corresponding to said plurality of light conduits so as to reproduce alphanumeric characters upon selective activation of the light-emitting diodes.

2. An apparatus according to claim 1, wherein each of the light conduits includes an elongate projection extending from the rear of the display.

3. An apparatus according to claim 1, wherein each of the light conduits includes an elongate hole extending within a moulded body of the display.

4. An apparatus according to claim 1, wherein the display surface is partially masked by an opaque layer provided adjacent the display surface of the at least one switch.

5. An apparatus according to claim 4, wherein a layer of light transmissive material overlies said opaque layer.

6. An apparatus according to claim 1, wherein the apparatus further includes means responding to switch operation to cause display of said information by said at least one switch.

7. An apparatus according to claim 1, wherein the at least one switch includes a plurality of such switches, and the apparatus further includes means responding to operation of at least one of said plurality of said switches to cause display of said information by at least another of said plurality of switches.

8. An apparatus according to claim 1, are Wherein said information includes information on at least one of patient usage time and pressure settings of the apparatus.

9. The apparatus according to claim 1, wherein the switch operating member is provided nth seven of said light conduits, each of said seven light conduits being provided with a respective one of said plurality of light-emitting diodes.

* * * * *

UNITED STATES PATENT AND TRADEMARK OFFICE
CERTIFICATE OF CORRECTION

PATENT NO.    : 6,339,421 B1
DATED         : January 15, 2002
INVENTOR(S)   : Puckeridge It is certified that error appears in the above-identified patent and that said Letters Patent is hereby corrected as shown below:

<u>Title page,</u>
Item [30], Foreign Application Priority Data, please change the Australian Priority Application No. from "PP4931" to -- PP4961 --.

Signed and Sealed this

Third Day of September, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.     : 6,339,421 B1
DATED          : January 15, 2002
INVENTOR(S)    : Puckeridge It is certified that error appears in the above-identified patent and that said Letters Patent is hereby corrected as shown below:

<u>Title page,</u>
Item [57], ABSTRACT, please correct ABSTRACT to read as follows:

-- An apparatus for administering continuous positive airway pressure to a patient includes a housing, a switch provided on the housing, and a graphical display. The graphical display includes a matrix of surface-mounted light-emitting diodes mounted on a printed circuit board for selective illumination in response to information generated by operation of the apparatus. A display which may include an electrical switch of the apparatus or display panel, has a light emitting display surface and a plurality of light conduits transmitting light from a respective portion of the LED matrix to a portion of the display device. The information generated by operation of the device is graphically displayed by the display device. --

Signed and Sealed this

Twenty-ninth Day of April, 2003

JAMES E. ROGAN
*Director of the United States Patent and Trademark Office*